United States Patent
Large

[11] 3,992,447
[45] Nov. 16, 1976

[54] ACARICIDAL AND LEPIDOPTERICIDAL ACTIVE CARBON-IMIDOTHIOATES

[75] Inventor: George B. Large, Pinole, Calif.

[73] Assignee: Stauffer Chemical, Westport, Conn.

[22] Filed: Oct. 20, 1975

[21] Appl. No.: 623,844

[52] U.S. Cl. .............................. 260/564 E; 424/326
[51] Int. Cl.² ........................................ C07C 123/00
[58] Field of Search .............................. 260/564 E

[56] References Cited
UNITED STATES PATENTS
2,849,306  8/1958  Searle ........................... 260/564 E FOREIGN PATENTS OR APPLICATIONS
675,916  12/1968  South Africa .................. 260/564 E
945,808  1/1964  United Kingdom ............. 260/564 E Primary Examiner—Gerald A. Schwartz
Attorney, Agent, or Firm—Michael J. Bradley

[57] ABSTRACT

Carbon-imidothioates having the formula

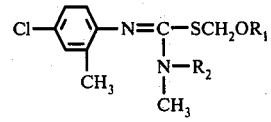

wherein $R_1$ is selected from the group consisting of alkyl containing from 1 to 4 carbon atoms, alkynyl containing from 1 to 4 carbon atoms, alkoxy alkylene containing from 2 to 4 carbon atoms and benzyl, and $R_2$ is either —$CH_3$ or —H, are active acaricides and lepidoptericides which can be applied to acarids or lepidoptera at any stage of development.

12 Claims, No Drawings

ACARICIDAL AND LEPIDOPTERICIDAL ACTIVE CARBON-IMIDOTHIOATES

DESCRIPTION OF THE INVENTION

The present invention is novel carbon-imidothioates which are active acaricides and lepidoptericides. The compounds of the present invention are represented by the formula:

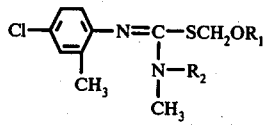

wherein $R_1$ is selected from the group consisting of alkyl containing from 1 to 4 carbon atoms, alkynyl containing from 1 to 4 carbon atoms, alkoxy alkylene containing from 2 to 4 carbon atoms and benzyl, and $R_2$ is either $-CH_3$ or $-H$. The compounds of this invention are effective acaricides and lepidoptericides when applied to the habitat of acarids and lepidoptera in acaricidally and lepidoptericidally effective amounts.

By "acaricidally or lepidoptericidally effective amount" is meant the amount of the herein disclosed acaricidal or lepidoptericidal compounds which when applied to the habitat of acarids or lepidoptera in any conventional manner will kill or substantially injure a significant portion of the population thereon.

The compounds of this invention can be generally prepared by reacting NaH with N-(4-chloro-2-methylphenyl)-N',N' dimethyl thiourea or (4-chloro-2-methylphenyl)-N'-methyl thiourea in a solvent such as tetrahydrofuran (THF) followed by reacting the reaction product with a compound having the formula $ClCH_2OR_1$ where $R_1$ is as defined above.

Preparation of the specific compounds of this invention is illustrated by the following examples:

EXAMPLE 1

S-Propargyloxymethyl-N-(4-chloro-2-methylphenyl)-N',N'-dimethyl isothiourea

To a slurry of NaH (0.36 g, 0.015 moles) in 75 ml of anhydrous THF (5.7 g, 0.015 moles) N-(4-chloro-2-methylphenyl)-N',N'-dimethyl thiourea was added portionwise and with stirring until hydrogen ceased to evolve. A solution of chloromethyl propargyl ether (3.6 g, 0.015 moles) in 25 ml THF was added dropwise. The resulting mixture refluxed for thirty minutes and cooled. Any unreacted sodium hydride was eliminated by adding 10 ml of ethanol and stirring the reaction mixture for five minutes. The reaction mixture was then diluted with an equal volume of benzene, washed two times with 300 ml $H_2O$, and dried over anhydrous $MgSO_4$. Volatiles were then removed on a rotary evaporator to yield 4.4 grams of a clear liquid, $N_D^{30}$ 1.5665. Structure was confirmed by NMR and IR spectroscopy.

EXAMPLE 2

S-Ethoxymethyl-N-(4-chloro-2-methylphenyl)-N',N'-dimethyl isothiourea

The same procedure was used in Example 1 except chloromethyl ethyl ether was used in place of chloromethyl propargyl ether to yield 4.1 grams liquid, $N_D^{30}$ 1.5560. Structure was confirmed by NMR and IR spectroscopy.

EXAMPLE 3

S-Isobutoxymethyl-N-(4-chloro-2-methylphenyl)-N',N'-dimethyl isothiourea

To a slurry of NaH (0.48 grams, 0.02 moles) in 75 ml of anhydrous THF (4.3 g, 0.02 moles) N-(4-chloro-2-methylphenyl)-N'-methyl thiourea was added portionwise and with stirring until hydrogen ceased to evolve. A solution of chloro-methylisobutyl ether was added dropwise and the resulting mixture refluxed for thirty minutes and cooled. Any unreacted sodium hydride was eliminated by adding 10 ml of ethanol and stirring the reaction mixture for five minutes. The reaction mixture was then diluted with an equal volume of benzene, washed two times with 300 ml $H_2O$ and dried over anhydrous $MgSO_4$. Volatiles were then removed on a rotary evaporator to yield 5.3 grams of a clear liquid, $N_D^{30}$ 1.5555. Structure was confirmed by NMR and IR spectroscopy.

Other compounds can be prepared in an analogous manner, starting with the appropriate materials as outlined above. Following is a table of compounds representative of those embodied in the present invention. Compound numbers have been assigned to them and are used for identification throughout the balance of this specification.

TABLE I

| Compound Number | $R_1$ | $R_2$ |
|---|---|---|
| 1 | $-CH_2-C_6H_5$ (benzyl) | $-CH_3$ |
| 2 | $-CH_2C\equiv CH$ | $-CH_3$ |
| 3 | $-CH_2CH_3$ | $-CH_3$ |
| 4 | $-CH_2CH_2Cl$ | $-CH_3$ |
| 5 | $-CH_2CH_2OCH_3$ | $-CH_3$ |
| 6 | $-CH_2CH=CH_2$ | $-CH_3$ |
| 7 | $-i-C_4H_9$ | $-CH_3$ |
| 8 | $-CH_2CH_3$ | $-H$ |
| 9 | $-CH_2CH_2Cl$ | $-H$ |
| 10 | $-CH_2CH=CH_2$ | $-H$ |
| 11 | $-CH_2CH(CH_3)_2$ | $-H$ |

LEPIDOPTERICIDAL EVALUATION

Compounds No. 1 through 11 were evaluated for lepidoptericidal activity on the Salt-Marsh Caterpillar as follows:

I. Salt-Marsh Caterpillar [*Estigmene acrea* (Drury)]: Leaf Dip Assay on Third Instar Salt-Marsh Caterpillar Larvae [*Estigmene acrea* (Drury)] — Test compounds are diluted in a 50—50 acetone-water solution. Sections of curly dock (*Rumex crispus*) leaves, approximately 1×1.5 inches, are immersed in the test solutions for 2–3 seconds and placed on a wire screen to dry. The dried leaves are placed in petri dishes containing a moistened piece of filter paper and infested with five second-instar salt-marsh larvae. Mortality of the larvae is recorded 48 hours later, and a piece of synthetic media is added to dishes containing survivors. These are then held for five additional days to observe for any delayed effects of the test chemicals.

Test concentrations range from 0.05% down to that at which approximately 50% mortality occurs.

Compounds No. 1 through 11 were evaluated for acaricidal activity on various acarid species as follows:

II. Two-Spotted Mite [*Tetranychus urticae* (Koch)]: Plant Dip Assay on Two-Spotted Mite [*Tetranychus urticae* (Koch)] — Pinto bean plants (*Phaseolus sp.*) approximately 10 cm tall, are transplanted into sandy loam soil in 3-inch clay pots and thoroughly infested with two-spotted mites of mixed ages and sexes. Twenty-four hours later, the infested plants are inverted and dipped for 2–3 seconds in 50—50 acetone-water solutions of the test chemicals. Treated plants are held in the greenhouse, and seven days later mortality is determined for both the adult mites and the nymphs hatching from eggs which were on the plants at the time of treatment. Test concentrations range from 0.05% down to that at which 50% mortality occurs.

III. Systemic Tests

A. Salt-Marsh Caterpillar:

Systemic Assay on Salt-Marsh Caterpillar Larvae [*Estigmene acrea* (Drury)] — Test chemicals are dissolved in acetone and aliquots are diluted in 200 cc of water in glass bottles. Two kidney bean plants (*Phaseolus vulgaris*), with expanded primary leaves, are supported in each bottle by cotton plugs so their roots and stems are immersed in the treated water. To each plant is then pinned a small mass of ready-to-hatch salt-marsh caterpillar eggs and the plants are placed in the greenhouse. Mortality is recorded after all control eggs have hatched and the young larvae are feeding on the plants. Test concentrations range from 10 ppm down to that at which approximately 50% mortality of the newly hatched larvae occurs.

B. Two-Spotted Mite:

Systemic Assay on Two-Spotted Mite [*Tetranychus urticae* (Koch)] — Test chemicals are dissolved in acetone and aliquots are diluted in 200 cc of water in glass bottles. Two pinto bean plants (*Phaseolus sp.*), with expanded primary leaves, are supported in each bottle by cotton plugs, so that their roots and stems are immersed in the treated water. The plants are then infested with 75–100 two-spotted mites of various ages and sexes. One week later the mortality of the adult mites and nymphs is recorded. Test concentrations range from 10 ppm down to that at which 50% mortality occurs.

The results by the above test procedures indicate in Table I the effective concentration at which an LD-50 control effect was achieved on the various species of lepidopterans and acarids.

TABLE II $$Cl-\underset{CH_3}{\underset{|}{\bigcirc}}-N=\underset{\underset{CH_3}{\underset{|}{N-R_2}}}{\overset{|}{C}}-SCH_2OR_1$$

| Compound Number | Contact | Syst | Ovicide | Eggs | PE |
|---|---|---|---|---|---|
| | SMC | | | 2SM | |
| | % | ppm | % | % | % |
| 1 | .05 | .02 | .003 | .002 | >.05 |
| 2 | .05 | .03 | .003 | .002 | >.05 |
| 3 | >.05 | .01 | .005 | .005 | >.05 |
| 4 | .05 | .1 | .005 | .03 | .03 |
| 5 | .05 | .3 | .005 | .03 | .03 |
| 6 | .05 | .03 | .003 | .008 | .03 |
| 7 | .05 | .1 | .01 | .003 | .01 |
| 8 | .05 | .1 | .01 | .01 | >.05 |
| 9 | >.05 | .3 | .05 | .03 | >.05 |
| 10 | >.05 | .2 | >.05 | .03 | .03 |
| 11 | .03 | .05 | .01 | .03 | .03 |

SMC=Salt-Marsh Caterpillar
2SM=Two-Spotted Mite
Syst=Systemic
PE=Post-embryonic
>=greater than The compounds of this invention are generally embodied into forms suitable for convenient application. For example, the compounds can be embodied into pesticidal compositions which are provided in the form of emulsions, suspensions, solutions, dusts and aerosol sprays. In general, such compositions will contain, in addition to the active compound, the adjuvants which are found normally in pesticide preparations. In these compositions, the active compounds of this invention can be employed as the sole pesticide component or they can be used in admixture with other compounds having similar utility. The pesticide compositions of this invention can contain, as adjuvants, organic solvents, such as sesame oil, xylene range solvents, heavy petroleum, etc.; water; emulsifying agents; surface active agents; talc; pyrophyllite; diatomite; gypsum; clays; propellants, such as dichlorodifluoromethane, etc. If desired, however, the active compounds can be applied directly to feedstuffs, seeds, etc., upon which the pests feed. When applied in such a manner, it will be advantageous to use a compound which is not volatile. In connection with the activity of the presently disclosed pesticidal compounds, it should be fully understood that it is not necessary that they be active as such. The purposes of this invention will be fully served if the compounds are rendered active by external influences, such as light or by some physiological action which occurs when the compounds are ingested into the body of the pest.

The precise manner in which the pesticidal compositions of this invention are used in any particular instance will be readily apparent to a person skilled in the art. Generally, the active pesticide compounds will be embodied in the form of a liquid composition, for example, an emulsion, suspension or aerosol spray. While the concentration of the active pesticide in the present compositions can vary within rather wide limits, ordinarily the pesticide compound will comprise not more than about 15.0% by weight of the compositions. Preferably, however, the pesticide compositions of this invention will be in the form of solutions or suspensions containing about 0.1 to 1.0% by weight of the active pesticide compound.

What is claimed is:

1. The compound having the formula

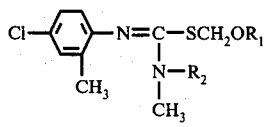

wherein $R_1$ is selected from the group consisting of alkyl containing from 1 to 4 carbon atoms, alkynyl containing from 1 to 4 carbon atoms, alkoxy alkylene containing from 2 to 4 carbon atoms and benzyl, and $R_2$ is either —$CH_3$ or —H.

2. The compound of claim 1 wherein $R_1$ is —$CH_3$ and $R_2$ is

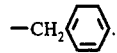

3. The compound of claim 1 wherein $R_1$ is —$CH_3$ and $R_2$ is —$CH_2C \equiv CH$.
4. The compound of claim 1 wherein $R_1$ is —$CH_3$ and $R_2$ is —$CH_2CH_3$.
5. The compound of claim 1 wherein $R_1$ is —$CH_3$ and $R_2$ is —$CH_2CH_2Cl$.
6. The compound of claim 1 wherein $R_1$ is —$CH_3$ and $R_2$ is —$CH_2CH_2OCH_3$.
7. The compound of claim 1 wherein $R_1$ is —$CH_3$ and $R_2$ is —$CH_2CH=CH_2$.
8. The compound of claim 1 wherein $R_1$ is —$CH_3$ and $R_2$ is —$i$—$C_4H_9$.
9. The compound of claim 1 wherein $R_1$ is —H and $R_2$ is —$CH_2CH_3$.
10. The compound of claim 1 wherein $R_1$ is —H and $R_2$ is —$CH_2CH_2Cl$.
11. The compound of claim 1 wherein $R_1$ is —H and $R_2$ is —$CH_2CH=CH_2$.
12. The compound of claim 1 wherein $R_1$ is —H and $R_2$ is —$CH_2CH(CH_3)_2$.

* * * * *